Figure 1:
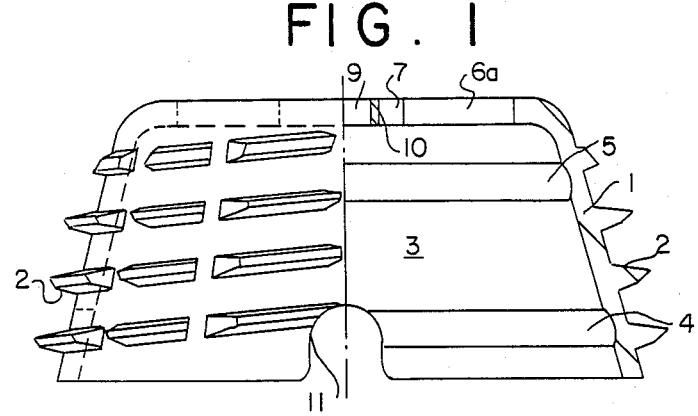

United States Patent [19]

Zweymuller et al.

[11] Patent Number: 4,919,676
[45] Date of Patent: Apr. 24, 1990

[54] METAL SHELL FOR AN ARTIFICIAL HIP JOINT SOCKET

[75] Inventors: K. Zweymuller, Vienna, Austria; Rudolf Koch, Berlingen, Switzerland

[73] Assignee: Sulzer Brothers Limited, Winterthur, Switzerland

[21] Appl. No.: 207,290

[22] Filed: Jun. 15, 1988

[30] Foreign Application Priority Data

Jun. 25, 1987 [CH] Switzerland .......................... 2398/87

[51] Int. Cl.$^5$ ................................................ A61F 2/34
[52] U.S. Cl. .................................................. 623/22
[58] Field of Search ........................ 623/16, 18, 22, 23

[56] References Cited

U.S. PATENT DOCUMENTS 3,685,058 8/1972 Tronzo .................................... 623/16
4,715,859 12/1987 Schelhas et al. ........................ 623/22

FOREIGN PATENT DOCUMENTS 2314708 10/1974 Fed. Rep. of Germany ........ 623/22
3406357 12/1984 Fed. Rep. of Germany .
2591471  6/1987 France ................................... 623/22
2598609 11/1987 France ................................... 623/22

Primary Examiner—David J. Isabella
Attorney, Agent, or Firm—Kenyon & Kenyon

[57] ABSTRACT

The outer shell possesses openings in the polar or apical region which serve to backfill the implanted shell with spongious bone material. The openings are separated by a web which extends through the axis of symmetry of the outer shell and which has a threaded bore to receive an insertion instrument. The instrument is centrally guided on an axial direction to facilitate control and alignment of the outer shell during insertion, especially in the case of outer shells to be screwed in with a self-cutting thread.

6 Claims, 1 Drawing Sheet

METAL SHELL FOR AN ARTIFICIAL HIP JOINT SOCKET

This invention relates to a metal shell for receiving a plastic socket element of an artificial hip joint socket for cementless anchoring in a pelvis.

Heretofore, it has been known, for example from U.S. Pat. No. 3,685,058 to use pins and nails on a hip joint socket for anchoring purposes and from French Patent 2,591,471 to use external threads for anchoring purposes. It has also been known from U.S. Pat. No. 4,596,580 to provide a hip joint socket for cementless anchoring in a pelvis which consists of an open outer shell and a plastic socket. The outer shell is formed as a ring which is open in the apical or polar region to permit the introduction and compaction of analogous or homologous bone material at the "bottom" of a surgically produced recess in the pelvis which receives the artificial hip joint socket. The open ring also permits backfilling of the annular outer shell with such material. This introduction of spongious tissue is the easier to carry out, the larger the openings are that exist for that purpose. Thus, in this construction, the outer shell is formed as a ring which covers only the walls of the artificial socket element leaving the entire polar region exposed. Further, it has been known from German O.S. 2,314,708 to provide a skeletal socket wherein an apical region is formed with a plurality of openings for penetration of bone cement.

In practice, it has now been found that implanting the annular outer shell, which often is provided on the exterior with a self-cutting thread, is relatively difficult, as there is no guidance in the direction of the socket axis by an insertion instrument centered on the pole or apex of the outer shell.

Accordingly, it is an object of the invention to provide an outer shell whose implantation is facilitated without unduly complicating the "filling in" of bone tissue into the "bottom" region of the surgical cutout in a pelvis.

It is another object of the invention to facilitate the implantation of apertured shells for a hip joint socket.

Briefly, the invention provides an outer metal shell for an artifical hip foint socket which comprises a peripheral wall to define a cavity to receive a plastic socket element and an opening in an apical region and a bridging means extending across the apical region to subdivide the opening while including a centrally disposed threaded bore for threadably receiving an insertion instrument.

Since the apertured shell has a centrally located bore, the insertion instrument can be disposed on the axis of symmetry of the shell so as to center the shell for implantation. In this manner, any change of direction of the instrument axis causes an identical change of direction of the shell axis so that alignment of the shell axis is greatly facilitated.

Moreover, particularly for outer shells with self-cutting threads, the position of the shell axis during cutting of the thread can be controlled continuously and, if necessary, corrected. Preferably, the bridging means is in the form of a single web to restrict the "open" area for introduction of spongiosa to only a minimal extent.

Figure 2:
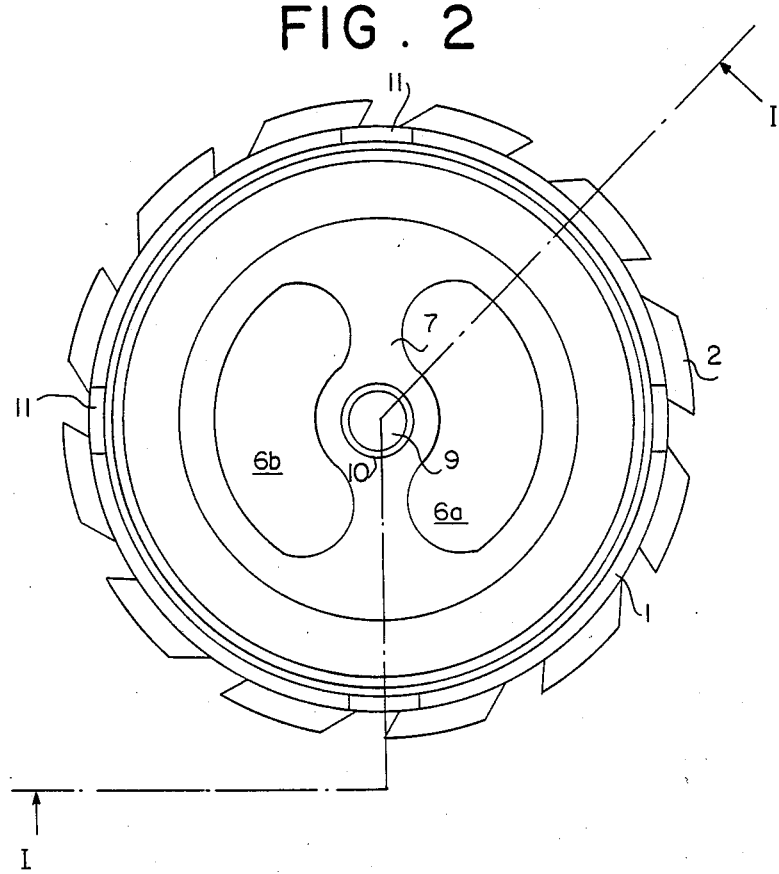

These and other objects and advantages of the invention will become more apparent from the following detailed description taken in conjunction with the accompanying drawings in which:

FIG. 1 illustrates a shell in accordance with the invention partially in section I—I of FIG. 2; and FIG. 2 represents a view of the shell of FIG. 1 from below.

Referring to FIG. 1 the outer metal shell 1 is formed of a peripheral wall which defines a cavity 3 for receiving a plastic socket element (not shown) as well as an opening in an apical region.

The wall of the shell 1 is basically in the form of a truncated cone. However, the shell may also be formed as a hemisphere or of other known form for an artificial hip joint socket. In addition, a self-cutting thread 2 is formed on the exterior surface of the wall of the shell 1.

The shell 1 is made of any suitable metal such as titanium or a titanium alloy. The cavity 3 is formed to receive a plastic socket element, for example an element formed of polyethylene, which contains the actual joint socket into which a spherical joint head of a femur head prosthesis (not shown) may fit. The connection of the shell 1 with the socket element (not shown) occurs near the equatorial edge of the prosthesis by means of a snap fit, such as described in European Patent Application 245527. To this end, an annular grove or depression 4 is formed in the wall of the shell 1 to receive a corresponding projection which extends out of the shell of the socket element in the direction from the pole to the equator. In addition, a cylindrical guide 5 is provided on the interior surface of the wall of the shell 1 inwardly of the groove 4. This cylindrical guide 5 serves to guide the socket element when the socket element is being driven or pressed into the shell 1 after the shell 1 has been secured within a bone. The guide 5, as described in the above noted European patent, cooperates with a cam which protrudes from the wall of the socket element which is circumferentially disposed on the socket element. This cam is sized to fit into the cylindrical guide 5 of the shell 1.

Referring to FIGS. 1 and 2, the apical region of the shell 1 is open toward the pelvis and a bridging means in the form of a single web 7 extends across the apical region to subdivide the opening into a pair of sub-openings 6a, 6b for receiving an ingrowth of bone tissue. As indicated in FIG. 2, each opening 6a, 6b is kidney-shaped. The web 7 which is integral with the peripheral wall is also provided with a bore 9 which is provided with an internal thread 10 and which is disposed on the axis of symmetry 8 of the shell 1. The threaded bore 9 is adapted to receive a threaded insertion instrument (not shown) by means of which the shell 1 can be screwed into a bone. In addition, four cutouts 11 are evenly distributed over the equatorial edge of the shell 1 to receive peg-type projections (not shown) of the socket element in order to prevent rotation of the socket element relative to the shell 1.

Referring to FIG. 2, the use of a single web 7 across the apertured apical region of the shell 1 maximizes the open space into which bone tissue may grow while at the same time providing the centrally disposed threaded bore 9 for receiving the insertion instrument.

In use, an insertion instrument (not shown) is threaded into the shell 1, for example from below as viewed in FIG. 1. The instrument is then used to screw the shell 1 into a pelvic bone. After implantation, the instrument can be removed and the socket element snap-fitted in place.

The bridging element may also be of another shape than a single web 7. For example, the bridging element may be Y-shaped.

The invention thus provides a shell for an artificial hip joint socket which can be guided in the direction of the socket axis by an insertion instrument centered on the axis of symmetry of the shell. Further, the invention provides for the implantation of the apertured shell into a pelvic bone in a simple manner.

What is claimed is:

1. An outer metal shell for an artificial hip joint socket, said shell comprising a peripheral wall defining a cavity for receiving a plastic socket element and having an opening in an apical region and a self-cutting thread on an exterior surface of said wall; and bridging means extending across said apical region to subdivide said opening into a plurality of subopenings to permit the introduction and compaction of bone material into a surgically produced recess in a pelvic bone, said means including a centrally disposed threaded bore for threadably receiving an insertion instrument.

2. A shell as set forth in claim 1 wherein said wall defines a truncated cone.

3. A shell as set forth in claim 1 wherein said bridging means includes a single web extending diametrically across said opening in said apical region.

4. A shell as set forth in claim 3 wherein said web is integral with said wall.

5. An outer shell for an artificial hip joint socket, said shell defining a cavity for receiving a plastic socket element, an opening in an apical region, a web extending across said apical region and including a centrally disposed threaded bore for threadably receiving an insertion instrument and a self-cutting thread on an exterior peripheral surface.

6. An outer shell for an artificial hip joint socket, said shell having a solid peripheral wall of truncated shape defining a cavity for receiving a plastic socket element, an opening in an apical region, a web extending across said apical region and including a centrally disposed threaded bore for threadably receiving an insertion instrument, and a self-cutting thread on an exterior of said wall.

* * * * *

UNITED STATES PATENT AND TRADEMARK OFFICE
CERTIFICATE OF CORRECTION

PATENT NO.  : 4,919,676

DATED       : April 24, 1990

INVENTOR(S) : K. ZWEYMULLER, et al

It is certified that error appears in the above-identified patent and that said Letters Patent is hereby corrected as shown below:

Column 1, line 45 "foint" should be -joint-

Signed and Sealed this

First Day of October, 1991

Attest:

HARRY F. MANBECK, JR.

*Attesting Officer*     *Commissioner of Patents and Trademarks*